US009285208B2

(12) United States Patent
Vemishetty

(10) Patent No.: US 9,285,208 B2
(45) Date of Patent: Mar. 15, 2016

(54) REAL-TIME RESAMPLING OF OPTICAL COHERENCE TOMOGRAPHY SIGNALS USING A FIELD PROGRAMMABLE GATE ARRAY

(71) Applicant: NATIONAL INSTRUMENTS CORPORATION, Austin, TX (US)

(72) Inventor: Kalyanramu Vemishetty, Austin, TX (US)

(73) Assignee: National Instruments Corporation, Austin, TX (US)

( * ) Notice: Subject to any disclaimer, the term of this patent is extended or adjusted under 35 U.S.C. 154(b) by 530 days.

(21) Appl. No.: 13/748,702

(22) Filed: Jan. 24, 2013

(65) Prior Publication Data

US 2014/0207418 A1 Jul. 24, 2014

(51) Int. Cl.
*G06F 17/00* (2006.01)
*G01B 9/02* (2006.01)
*G01N 21/47* (2006.01)
*A61B 5/00* (2006.01)

(52) U.S. Cl.
CPC ........ *G01B 9/02004* (2013.01); *G01B 9/02069* (2013.01); *G01B 9/02091* (2013.01); *G01N 21/4795* (2013.01); *A61B 5/0066* (2013.01)

(58) Field of Classification Search
CPC .... A61B 3/102; A61B 5/0066; A61B 3/1225; G01B 9/02091; G01B 9/62069; G01N 21/4795
USPC ............. 702/191; 250/459.1, 208.1; 356/497, 356/479; 382/128, 131
See application file for complete search history.

(56) References Cited

U.S. PATENT DOCUMENTS

| 7,903,256 | B2 | 3/2011 | Sarunic et al. |
| 8,233,152 | B2 | 7/2012 | Suehira |
| 8,348,427 | B2 | 1/2013 | Buckland et al. |
| 8,565,499 | B2 * | 10/2013 | Zhao et al. ................... 382/128 |

OTHER PUBLICATIONS

Van der Jeught et al.; "Real-time resampling in Fourier domain optical coherence tomography using a graphics processing unit;" Journal of Biomedical Optics, vol. 15(3), 030511, Jun. 3, 2010, retrieved from <http://biomedicaloptics.spiedigitallibrary.org/article.aspx?articleid=1103391> on May 28, 2013; pp. 1-3.

* cited by examiner

*Primary Examiner* — Carol S Tsai
(74) *Attorney, Agent, or Firm* — Meyertons Hood Kivlin Kowert & Goetzel, P.C.; Jeffrey C. Hood

(57) ABSTRACT

A signal processing system implemented on a Field Programmable Gate Array (FPGA) operates according to a low frequency K-Clock to sample Optical Coherence Topography (OCT) signals, as opposed to relying on a high frequency K-Clock to obtain the same information. A resampler is used to resample the OCT signal uniformly in the optical frequency domain. The resampling may be performed by extracting instantaneous phase information from a low-frequency digitized K-Clock signal, unwrapping the extracted phase information, multiplying the unwrapped extracted phase information with an interpolation factor to obtain recalculated phase information, determining one or more integer crossing points corresponding to the recalculated phase information, and interpolating one or more values of the OCT signal based on the one or more integer crossing points. The integer crossing points may represent points in phase divisible by 360 degrees, within the range of points in phase defined by the recalculated phase information.

26 Claims, 8 Drawing Sheets

MZI: Mach-Zehnder Interferometer

REAL-TIME RESAMPLING OF OPTICAL COHERENCE TOMOGRAPHY SIGNALS USING A FIELD PROGRAMMABLE GATE ARRAY

FIELD OF THE INVENTION

The present invention relates to the field of instrumentation, and more particularly to the design of optical coherence tomography systems.

DESCRIPTION OF THE RELATED ART

In many industrial applications (and others), instruments collect data or information from an environment or unit under test (UUT), and may also analyze and process acquired data. Some instruments provide test stimuli to a UUT. Examples of instruments include oscilloscopes, digital multimeters, pressure sensors, arbitrary waveform generators, digital waveform generators, etc. The information that may be collected by respective instruments includes information describing voltage, resistance, distance, velocity, pressure, oscillation frequency, humidity, and/or temperature, among others. Computer-based instrumentation systems typically include transducers for capturing a physical phenomenon and generating a representative electrical signal, signal conditioning logic to perform amplification on the electrical signal, isolation, and/or filtering, and analog-to-digital (A/D) conversion logic for receiving analog signals and providing corresponding digital signals to the host computer system.

In a computer-based system, the instrumentation hardware or device is typically an expansion board plugged into one of the I/O slots of the computer system. In another common instrumentation system configuration, the instrumentation hardware is coupled to the computer system via other means such as through a VXI (VME extensions for Instrumentation) bus, a GPIB (General Purpose Interface Bus), a PXI (PCI extensions for Instrumentation) bus, Ethernet, a serial port or bus, or parallel port of the computer system. The instrumentation hardware may include a DAQ (Data Acquisition) board, a computer-based instrument such as a multimeter, or another type of instrumentation device. In another common system configuration, a chassis and boards inserted in the chassis may operate as a standalone instrument or instrument suite, although in some cases a host computer may be used to configure or program the boards prior to, or during operation.

The instrumentation hardware may be configured and controlled by software executing on a host computer system coupled to the system, or by a controller card installed in the chassis. The software for configuring and controlling the instrumentation system typically includes driver software and the instrumentation application software, or the application. The driver software serves to interface the instrumentation hardware to the application and is typically supplied by the manufacturer of the instrumentation hardware or by a third party software vendor. The application is typically developed by the user of the instrumentation system and is tailored to the particular function that the user intends the instrumentation system to perform. The instrumentation hardware manufacturer or third party software vendor sometimes supplies application software for applications that are common, generic, or straightforward. Instrumentation driver software provides a high-level interface to the operations of the instrumentation device. The instrumentation driver software may operate to configure the instrumentation device for communication with the host system and to initialize hardware and software to a known state. The instrumentation driver software may also maintain a soft copy of the state of the instrument and initiated operations. Further, the instrumentation driver software communicates over the bus to move the device from state to state and to respond to device requests.

A wide variety of instrumentation systems exist for acquiring and processing optical signals. One specific method of optical signal acquisition and processing is Optical Coherence Tomography (OCT), an interferometric technique that makes use of near-infrared light to capture three-dimensional (3D) images from within optical scattering media, such as biological tissue for example, at micrometer-resolution. In general, interferometry refers to various techniques that involve the superimposing of waves in order to extract information about those waves. The use of relatively long wavelength light in OCT allows penetration into the scattering medium. Depending on the properties of the light source—which can be super luminescent diodes, ultra short pulsed lasers, or super continuum lasers among others—it is possible to achieve sub-micrometer resolution, with very wide-spectrum sources emitting over a ~100 nm wavelength range. A more recent implementation of OCT is frequency-domain OCT, which provides advantages in signal-to-noise ratio (SNR), and faster signal acquisition. Commercial OCT systems are typically used in art conservation and diagnostic medicine, especially in ophthalmology where the process is used to obtain detailed images from within the retina. OCT has also been used in interventional cardiology to help diagnose coronary artery disease.

One special class of OCT is Swept Source Optical Coherence Tomography (SS-OCT). A Swept Source Laser System (SSLS, or SS-OCT system) uses a laser that generates optical signals whose wavelength is swept over a narrow band. The optical signal is then split into a reference arm and a sample arm by an optical beam splitter, and the reflections from the sample arm and the reference arm are combined by an optical combiner to produce interference/fringe patterns. The interference patterns are converted into electronic signals by a photo detector, and a digitizer is used to record these resulting electronic signals (e.g. to produce a digital representation of those electronic signals).

One drawback of a Swept Source Laser (SSL) is that it exhibits non-linearities in the optical frequency domain. In order to compensate for these non-linearities, a clock signal (K-Clock) is generated to indicate non-linearities in the frequency sweep of the optical signal. The K-Clock is uniform in the optical frequency domain but not in the time domain, and can be used as a sampling clock for compensating for the non-linearities in the optical signal. The K-Clock can be generated internal or external to the laser, using an interferometric setup. In order to image deeper depths with greater resolution, a high speed K-Clock is typically required. However, creating a high-frequency K-Clock with an interferometric setup is challenging, as the fringe patterns generated by an interferometric setup at deeper depths degrade as they exceed the coherence length of the laser (in other words, as they exceed the propagation distance from the source of the laser to a point where the laser maintains a specified degree of coherence).

Other corresponding issues related to the prior art will become apparent to one skilled in the art after comparing such prior art with the present invention as described herein.

SUMMARY OF THE INVENTION

Various embodiments of the invention include a signal processing system implementing a resampling approach on a Field Programmable Gate Array (FPGA), which operates according to a low frequency K-Clock to sample OCT signals, as opposed to relying on a high frequency K-Clock to obtain the same information. Traditional systems that perform sampling of OCT signals typically use a K-Clock that is external to the digitizer. Such a setup however requires the K-Clock frequency to be higher than the maximum frequency of the OCT signal by a factor of at least two (2). The K-Clock signal fringe quality degrades as the optical delay between the two arms that produce the interference pattern increase. Such is the case, for example, when a high frequency fringe pattern such as a K-Clock needs to be generated. Another approach to solve this problem includes compensating for the non-linearities in software. These approaches use off-line processing of the data to linearize the OCT Signal in K-space by collecting the K-Clock signal once, or using a pre-recorded K-Clock signal. This approach also has its limitations, since the laser sources are unstable and drift over time, which results in a variance of the signal properties of the K-Clock signal.

In a new inline processing algorithm, the OCT Signal may be oversampled with a low-frequency K-Clock. As mentioned earlier, the K-Clock is uniform in the optical frequency (wave-number) domain and non-uniform in the time-domain. An OCT signal acquired using a free-running internal clock of a digitizer is uniform in the time-domain and non-uniform in the optical frequency domain. Therefore, a resampler may be used to resample the OCT signal uniformly in the optical frequency domain. Accordingly, one advantage of various embodiments of the SS-OCT system disclosed herein is the elimination of the need for a high frequency K-Clock, which is required in present day systems when imaging at deeper axial depths within tissues and materials. The embodiments also present a real-time processing solution with low latency for resampling, and make it useful for implementation on embedded platforms such as an FPGA. The need for additional hardware circuitry to provide an external K-Clock for analog-to-digital conversion (ADC) is therefore also eliminated.

Accordingly, a method for performing optical coherence tomography (OCT) may include extracting phase information (which may be normalized phase information) from a control signal, unwrapping the extracted phase information, multiplying the unwrapped extracted phase information with an interpolation factor to obtain recalculated phase information, determining one or more integer crossing points corresponding to the recalculated phase information, and interpolating one or more values of the OCT signal according to the determined one or more integer crossing points. The control signal may be a discrete signal (or discrete-time signal), which may be obtained by digitizing an analog signal that is a sinusoidal signal with varying frequency over time. The phase information of the control signal may be extracted by performing a filtering operation on the control signal, where the filtering operation includes performing a Hilbert transformation on the control signal, phase shifting the control signal, and/or reducing distortion and noise in the control signal. The extracting, unwrapping, multiplying, determining, and interpolating operations may all be performed in real-time, with various operations overlapping with each other when sufficient information is present for each given operation to be performed.

In some embodiments, logic gates in an FPGA may be interconnected (i.e. programmed) to perform SS-OCT operations. Thus, the FPGA may be operated to extract phase information from a control signal, unwrap the extracted phase information, multiply the unwrapped extracted phase information with an interpolation factor to obtain recalculated phase information, determine one or more integer crossing points corresponding to the recalculated phase information, and interpolate one or more values of an incoming OCT signal according to the determined one or more integer crossing points. The FPGA may further be operated to extract the phase information from the control signal by filtering the control signal, which may include a Hilbert transformation on the control signal, phase shifting the control signal, and/or reducing distortion and noise in the control signal. The control signal may be a digitized version of an analog sinusoidal signal whose frequency varies over time.

Based on the above, a method for processing a data signal may include identifying equally spaced points in phase of a control signal, where each identified point in phase corresponds to a respective pair of values of the data signal, and resampling the data signal according to the identified equally spaced points in phase of the control signal. The resampling is performed for each identified point in phase, and includes linearly interpolating a corresponding value of the data signal between the respective pair of values of the data signal corresponding to the identified point in phase. In some embodiments, the equally spaced points in phase are identified by extracting phase information from the control signal, obtaining points in phase from the extracted phase information, multiplying each obtained point in phase with an interpolation factor to obtain recalculated points in phase—with the recalculated points in phase defining a range of recalculated points in phase—and identifying desired points in phase within the range of recalculated points in phase. Each desired point is evenly divisible by a specified number, e.g. 360 degrees, and has a value that falls between respective values of a corresponding pair of recalculated points in phase within the range of recalculated points in phase, and represents one of the identified equally spaced points in phase. Identifying the equally spaced points in phase of the control signal and the resampling of the data signal may be performed in real-time, and at least a portion of the identifying may be performed concurrently with the resampling operation.

In one set of embodiments, a system configurable to perform SS-OCT may include a first logic element to extract phase information, e.g. instantaneous phase information from a control signal, a second logic element to obtain phase points from the extracted (instantaneous) phase information, a third logic element to multiply each obtained phase point with an interpolation factor to obtain recalculated phase points, a fourth logic element to identify desired phase points within a range defined by the recalculated phase points, and a fifth logic element to resample an incoming signal according to the identified desired phase points, where each desired phase point is evenly divisible by a specified number (e.g. 360 degrees), and has a value that falls between respective values of a corresponding pair of recalculated phase points within the range defined by the recalculated phase points. The first logic element may include a bandpass filter, and/or a Hilbert Transform implemented as a finite impulse response filter.

In order to extract the phase information, the first logic element may first obtain a representation of the control signal as a complex function, and obtain the phase information based on an imaginary component of the representation of the control signal and a delayed version of the control signal. The system may also include circuitry to generate the control signal, and in at least one embodiment, the circuitry includes a first signal generator to generate an analog signal, and an analog-to-digital converter to generate the control signal by digitizing the analog signal. The analog signal may be a sinusoidal signal with varying frequency over time. When performing OCT, the incoming signal is an OCT signal, and the control signal is a K-Clock signal. At least the first, second, third, fourth, and fifth logic elements of the system may be implemented on an FPGA, and may perform their respective operations inline and in real-time.

Other aspects of the present invention will become apparent with reference to the drawings and detailed description of the drawings that follow.

BRIEF DESCRIPTION OF THE DRAWINGS

A better understanding of the present invention can be obtained when the following detailed description of the preferred embodiment is considered in conjunction with the following drawings, in which.

Figure 1:
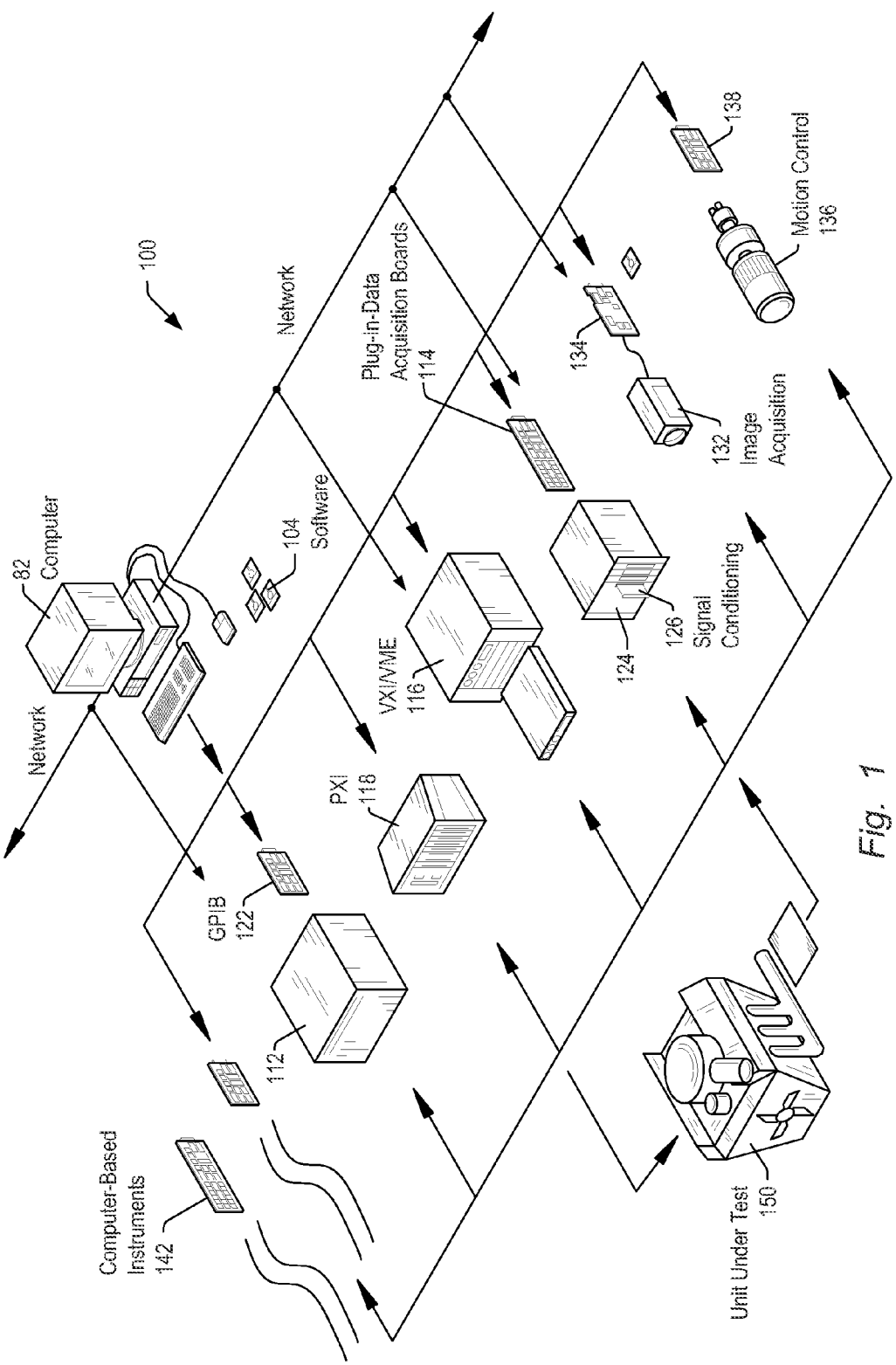
FIG. 1 shows an instrumentation control system with instruments networked together according to one embodiment of the invention.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE EMBODIMENTS

Embodiments of the present invention may be used in systems configured to perform test and/or measurement functions, or to model and simulate functions, e.g., modeling or simulating a device or product being developed or tested, etc. More specifically, it may be used in applications requiring optical signal acquisition and processing for performing high resolution 3-dimensional (3D) imaging from within optical scattering media. However, it is noted that the present invention may equally be used for a variety of applications, and is not limited to the specific applications disclosed herein. In other words, applications discussed in the present description are exemplary only, and the present invention may be used in any of various types of systems. Thus, the system and method of the present invention may be used in any number of different applications.

It should be noted that as used herein, "normalized phase information" refers to phase information (in degrees) divided by 360 degrees. It should be further noted that the normalized phase information may be expressed in radians as phase information obtained through a Hilbert transformation and then divided by $2\pi$. Furthermore, the instantaneous phase of a signal is interpreted as the arctangent of the ratio of the imaginary component and the real component of a complex representation of the signal (i.e., instantaneous phase=arctan (imaginary component/real component)). Accordingly, the value of the instantaneous phase is understood to vary between $-\pi$ and $\pi$, leading to discontinuities in phase calculation. As used herein, "phase unwrapping" refers to the process of accumulating the phase whenever a discontinuity occurs in the instantaneous phase signal.

It should further be noted that the various terms or designations for circuits/components and signals as they appear herein, for example in such expressions as "driver circuit", "delay circuit", "data signal", "control signal", etc. are merely names or identifiers used to distinguish among the different circuits/components and/or between different signals, and these terms are not intended to connote any specific meaning, unless otherwise indicated. Finally, a "discrete signal" or "discrete-time signal" is intended to mean a signal composed of a sequence of discrete values, in contrast to a continuous-time signal or analog signal, which has continuous amplitude over time. A discrete-time signal may have been obtained by sampling a continuous-time signal, in which case each value in the discrete signal is referred to as a sample. Accordingly, a discrete signal may be a digitized analog signal.

FIG. 1 illustrates an exemplary instrumentation control system 100 which may be configured according to embodiments of the present invention. System 100 comprises a host computer 82 which may couple to one or more instruments configured to perform a variety of functions using timing control implemented according to various embodiments of the present invention. Host computer 82 may comprise a CPU, a display screen, memory, and one or more input devices such as a mouse or keyboard as shown. Computer 82 may operate with one or more instruments to analyze, measure, or control a unit under test (UUT) or process 150. The one or more instruments may include a GPIB instrument 112 and associated GPIB interface card 122, a data acquisition board 114 inserted into or otherwise coupled with chassis 124 with associated signal conditioning circuitry 126, a VXI instrument 116, a PXI instrument 118, a video device or camera 132 and associated image acquisition (or machine vision) card 134, a motion control device 136 and associated motion control interface card 138, and/or one or more computer based instrument cards 142, among other types of devices.

The computer system may couple to and operate with one or more of these instruments. In some embodiments, the computer system may be coupled to one or more of these instruments via a network connection, such as an Ethernet connection, for example, which may facilitate running a high-level synchronization protocol between the computer system and the coupled instruments. The instruments may be coupled to the unit under test (UUT) or process 150, or may be coupled to receive field signals, typically generated by transducers.

System 100 may be used in a data acquisition and control applications, in a test and measurement application, an image processing or machine vision application, a process control application, a man-machine interface application, a simulation application, or a hardware-in-the-loop validation application, among others.

Figure 2:
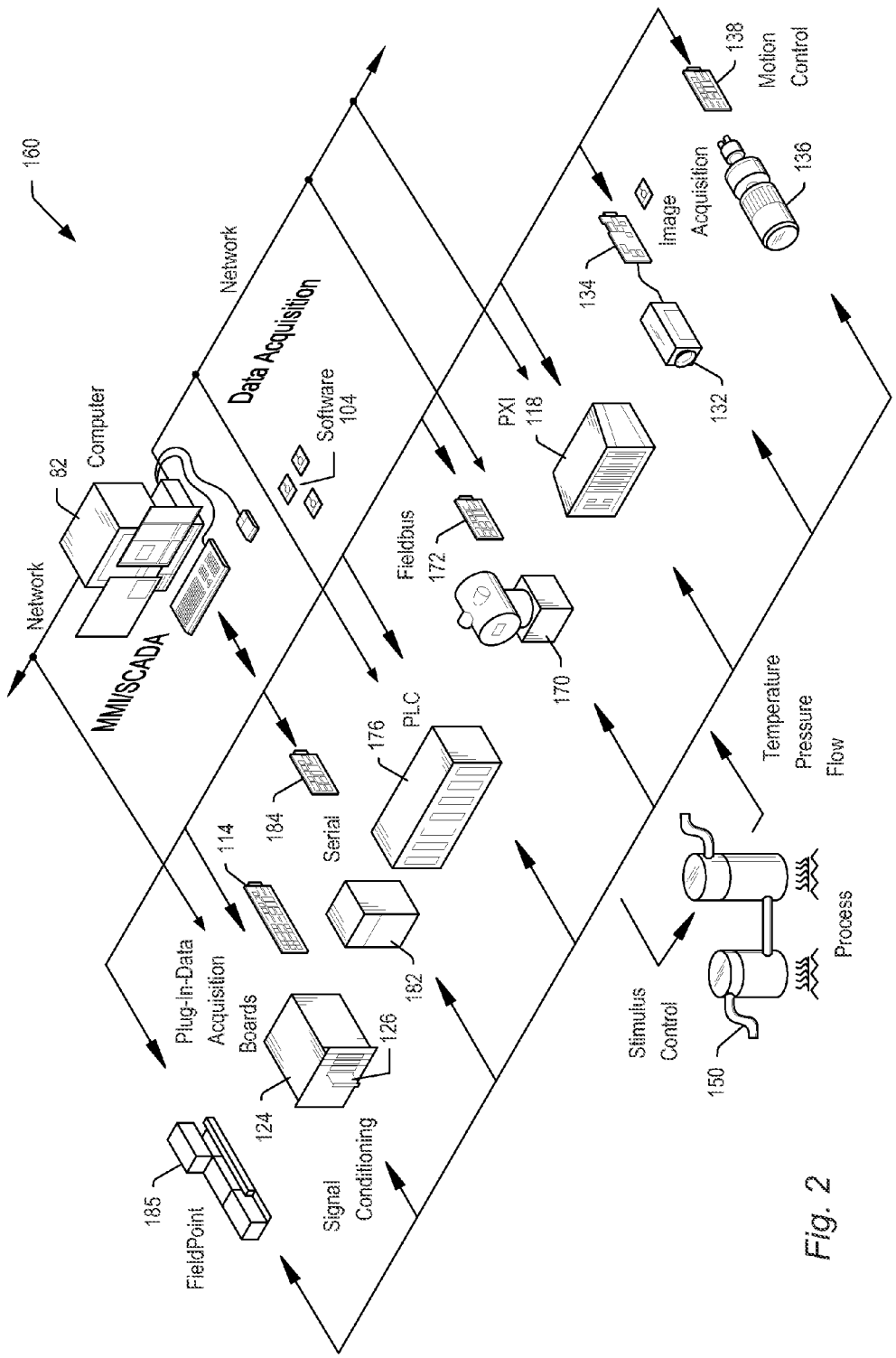
FIG. 2 shows an industrial automation system with instruments networked together according to one embodiment of the invention.

FIG. 2 illustrates an exemplary industrial automation system 160 that may be configured according to embodiments of the present invention. Industrial automation system 160 may be similar to instrumentation or test and measurement system 100 shown in FIG. 2A. Elements that are similar or identical to elements in FIG. 1 have the same reference numerals for convenience. System 160 may comprise a computer 82 which may couple to one or more devices and/or instruments configured to perform a variety of functions using timing control implemented according to various embodiments of the present invention. Computer 82 may comprise a CPU, a display screen, memory, and one or more input devices such as a mouse or keyboard as shown. Computer 82 may operate with the one or more devices and/or instruments to perform an automation function, such as MMI (Man Machine Interface), SCADA (Supervisory Control and Data Acquisition), portable or distributed data acquisition, process control, and advanced analysis, among others, on process or device 150.

The one or more devices may include a data acquisition board 114 inserted into or otherwise coupled with chassis 124 with associated signal conditioning circuitry 126, a PXI instrument 118, a video device 132 and associated image acquisition card 134, a motion control device 136 and associated motion control interface card 138, a field bus device 170 and associated field bus interface card 172, a PLC (Programmable Logic Controller) 176, a serial instrument 182 and associated serial interface card 184, or a distributed data acquisition system, such as the Compact FieldPoint or CompactRIO systems available from National Instruments, among other types of devices. In some embodiments, similar to the system shown in FIG. 1, the computer system may couple to one or more of the instruments/devices via a network connection, such as an Ethernet connection.

Figure 3:
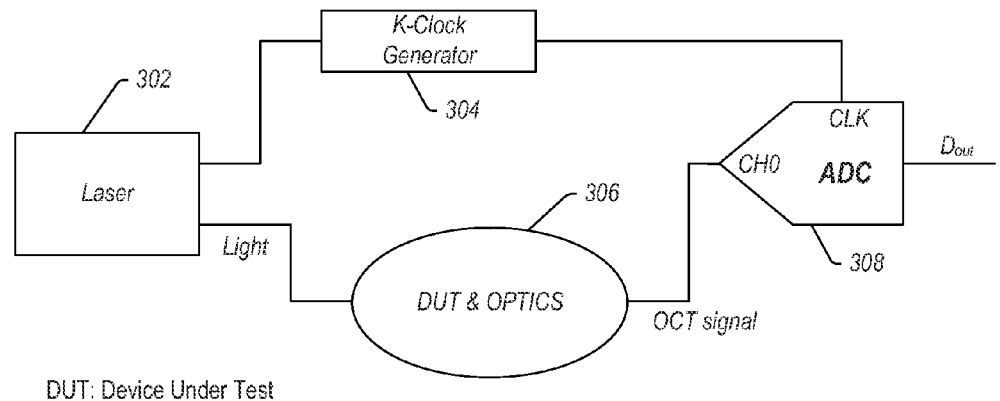
FIG. 3 shows the simplified block diagram of a prior art optical coherence tomography (OCT) system.

System 100 and/or 200 may be used for optical signal acquisition and processing through Optical Coherence Tomography (OCT), according to one set of embodiments. For example, referring to FIG. 1, devices 124, 126 and 114 may be adapted as part of a subsystem performing Swept Source Optical Coherence Tomography (SS-OCT). The simplified block diagram of a basic prior art SS-OCT system is shown in FIG. 3. A Laser 302 is used to generate the light, which is guided through various optics for performing the imaging on the "device under test" (DUT). The optics and DUT are shown in a single block 306 for ease of illustration. The resulting OCT signal is then provided to an input channel CH0 of ADC 308, which is clocked at its CLK port with a K-Clock signal 304 generated based on Laser 302. ADC then provides the digital output $D_{out}$, representative of the OCT signal. As seen in FIG. 3, K-Clock 304 is external to ADC 308, and is a high-frequency clock, running in the range of 1 GHz, for example. Typically, the OCT Signal is sampled on the zero-crossings of the K-Clock 304, as they are uniformly spaced in the optical frequency domain.

Figure 4:
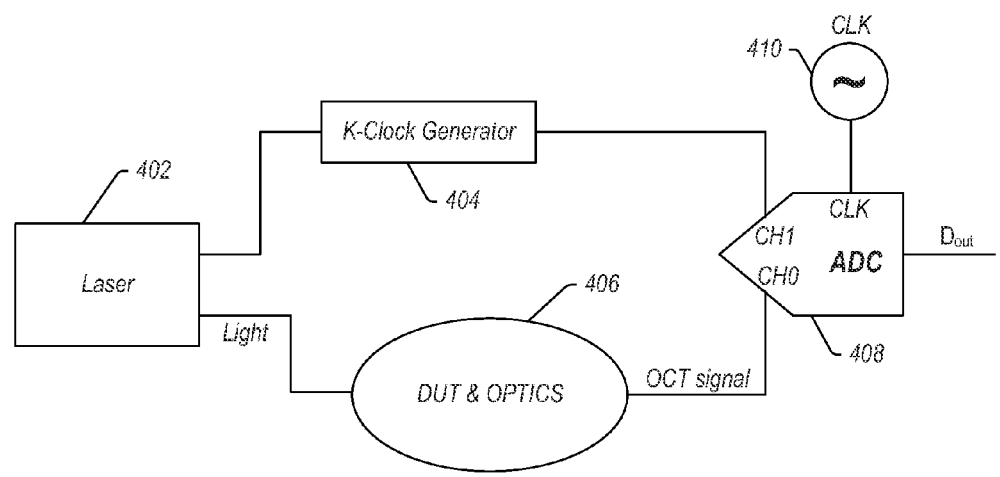
FIG. 4 shows the simplified block diagram of a prior art OCT system that performs resampling.
Figure 5:
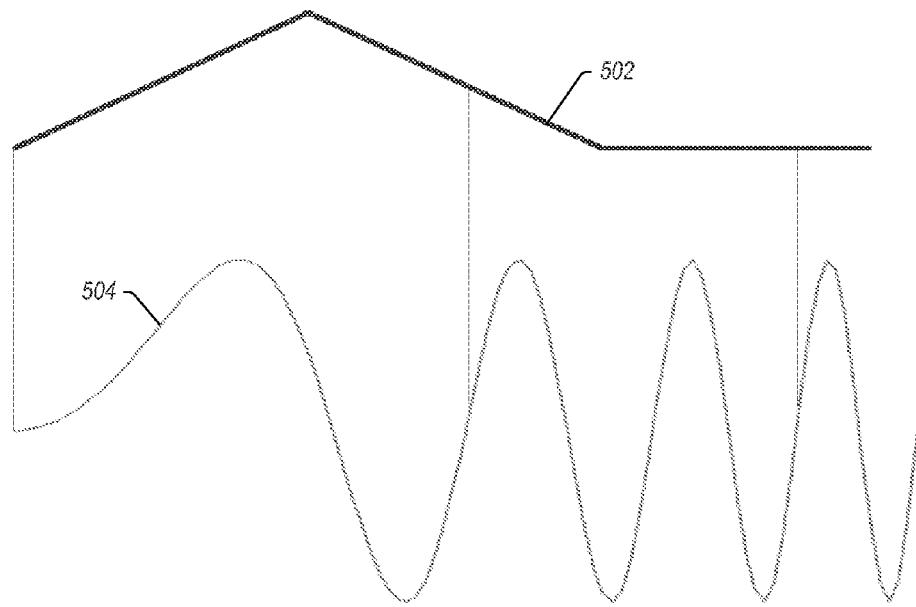
FIG. 5 shows a signal diagram illustrating resampling of an OCT signal using a variable frequency K-Clock, with a resampling factor of 1.

The simplified block diagram of a basic prior art SS-OCT system in which the OCT signal is resampled at the K-Clock zero-crossing domain is shown in FIG. 4. As seen in FIG. 4, the difference between the SS-OCT of FIG. 3 and the SS-OCT of FIG. 4 is the difference between the clocking configuration of ADC 308 and ADC 408. While ADC 308 is clocked with a high-frequency K-Clock signal at its CLK port, ADC 408 receives an internal K-Clock signal 404 at a second input port CH1, and is clocked with an external clock signal 410. K-Clock signal 404 is also generated based on Laser 402. In this scenario, K-Clock signal generator 404 may use an interferometer and a balanced detector to generate the K-Clock signal, with the balanced detector outputting the K-Clock signal as an analog chirp signal, which will be further described below. Accordingly, the frequency of K-Clock signal 404 is varied, and as shown in the corresponding timing diagram in FIG. 5, resampling the OCT signal 502 at the K-Clock 504 zero-crossing and rising edge yields an OCT Signal in uniform domain. The method illustrated in FIGS. 4 and 5 is similar to sampling the OCT Signal by using external K-Clock signal 304 as shown in FIG. 3, but it still has the disadvantage of requiring the K-Clock signal 404 to be at least twice as fast as the OCT Signal. In general, when performing OCT, varying the imaging depth requires changing the frequency of the K-Clock signal, which makes it cumbersome and impractical to use a K-Clock external to the ADC (such as K-Clock 304 to ADC 308 in FIG. 3), since the optical setup has to be changed every time imaging at different (or deeper) depths is desired.

Figure 6:
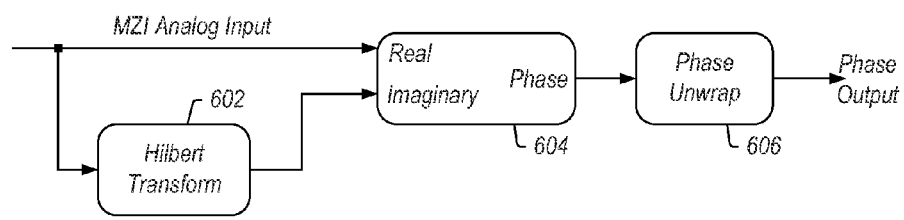
FIG. 6 shows a function diagram illustrating traditional phase unwrapping operation.

Even though, sampling the OCT Signal at the zero-crossing of K-Clock (as illustrated in FIGS. 4 and 5) is widely used, the resampling may be performed in software, which extends the technique of zero-crossing by resampling the OCT signal on zero-crossings as well as other uniformly spaced points in the optical frequency (K-Clock) domain. One approach that may be used to find uniformly spaced points in optical frequency domain is through the use of a Hilbert Transform followed by Phase unwrapping, as shown in FIG. 6. In signal processing, the Hilbert transform is typically used to derive the analytic representation of a signal, that is, the representation of the signal as a complex (analytic) function. Thus, the analog signal input is provided to a Hilbert Transform 602, and the imaginary portion of the analytic representation of the MZI signal may be used together with the MZI signal to obtain a phase component as illustrated in function block 604, and the phase component may then be unwrapped as illustrated in function block 606 to obtain a phase output. This approach works great for post-processing (i.e. processing once all required data has been acquired), but is difficult to realize as an inline real-time processing system (i.e. where processing is performed concurrently in a pipelined manner while new samples and data are being acquired).

Various embodiments disclosed herein are directed to realizing the overall technique illustrated in FIG. 6 in a real-time, inline processing system, making it possible to efficiently implement SS-OCT using real-time processing devices, such as a field programmable gate array (FPGA) for example. In order to make the algorithm suitable for real-time inline processing, the OCT signal may be interpolated at instances where the integer portion of the value of the phase changes. Furthermore, the phase may be multiplied with a constant integer to obtain integer indices at which the OCT signal may be interpolated, and the interpolation may be performed at those integer indices. The concept of multiplying the phase with a constant integer is referred to as "Phase Oversampling".

Figure 7:
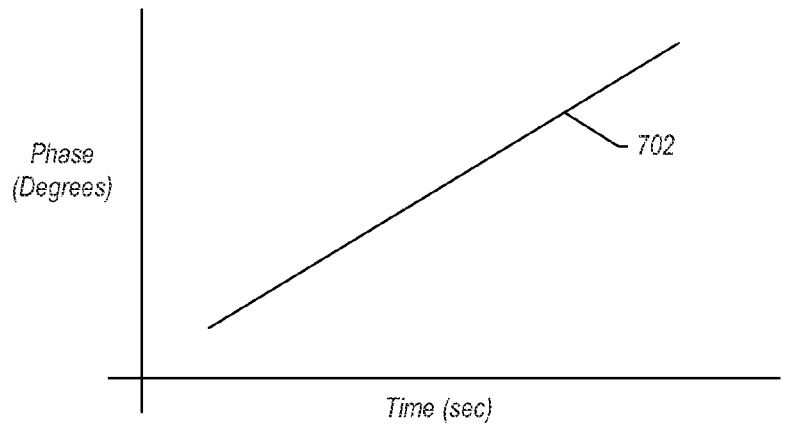
FIG. 7 shows a signal diagram illustrating phase variation of a sinusoidal signal over time.
Figure 8:
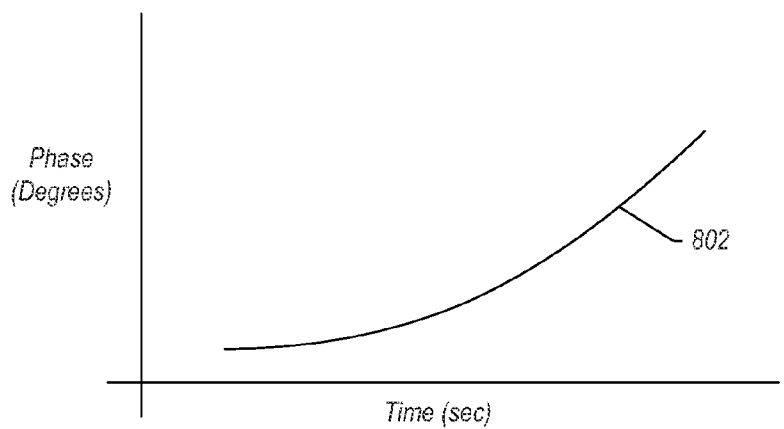
FIG. 8 shows a signal diagram illustrating phase variation of a chirp signal over time.

For purposes of illustration, the simple example may be considered where the K-Clock is a sinusoidal signal. The phase of this signal looks similar to the phase/time relationship shown in the function diagram of FIG. 7. As seen in FIG. 7, the phase varies linearly over time, as illustrated by line 702. In practice, the K-Clock signal may be implemented as a chirp signal, i.e., a sinusoidal signal with varying frequency over time. The phase relationship of such a chirp signal resembles that of curve 802 shown in FIG. 8. As shown in FIG. 8, the phase varies quadratically over time, as illustrated by curve 802. In order to better understand this resampling technique, it is important to examine the phase variation of the K-Clock signal over time.

In order to illustrate the K-Clock based resampling, a simple data set may be considered. For example, the data set may include OCT signal values of [0.1, −0.1, 1.2, 3.4, −5.6] Volts, for which the corresponding phases of K-Clock include the phase values of [41, 81, 141, 221, 320] degrees. That is, for the data set of OCT signal values presented above, the phase of K-Clock varies from 41 deg to 321 degrees over a period of 5 sampled points. To extract the image for OCT analysis, the OCT signal would have to be resampled at equally spaced points in phase (or, in other words, at equally spaced phase points). For the given data set above, the equally spaced phase interval between 41 degrees and 321 degrees may be expressed as: (Final Value-Initial Value)/(Required Number of Resampled Points-1), which, for the example above, would result in the numerical value of (321 degrees-41 degrees)/4=70 degrees. Thus, the phase points of interest are: [41, 41+70, 41+2*70, 41+3*70, 41+4*70] degrees=[41, 111, 181, 251, 321] degrees. The OCT signal may be reevaluated (or resampled) at these points, using linear interpolation.

However, this may present a problem for inline resampling when attempting to calculate the phase points (or phase values) at which to resample the data in real-time, because the end phase point (321 degrees in the example above) is not known ahead of time. To overcome this problem, the data values may be resampled at phase points that are multiples of 360 degrees, or integer multiples of $2\pi$ in radians. As previously mentioned, dividing by 360 degrees a phase value given in degrees yields a corresponding phase value in radians, which is also referred to herein as "normalized phase value". In the above example, there aren't any phase points where the phase value is a multiple of 360 degrees. This may be overcome however, by introducing a "Phase Oversample Factor", or "Interpolation Factor". Accordingly, new resample phase points may be designated as the locations where the multiple of the phase and the phase Interpolation Factor (i.e., phase*Interpolation Factor) is a multiple of 360 degrees. For the above example, for an Interpolation Factor of '5', the recalculated phase values are: [41*5, 81*5, 141*5, 221*5, 321*5] degrees=[205, 405, 705, 1105, 1605] degrees.

In the range of recalculated phase point values, the phase values of interest are: [360, 720, 1080, 1440] degrees, which are the values divisible by 360 within that range. The OCT signal at the recalculated phase of 360 degrees is then obtained as the linear interpolation of the OCT signal between phase points [205, 405] degrees, i.e., a value of the OCT signal obtained by linear interpolation from the OCT signal values of [0.1, −0.1]. Similarly, the signal at the recalculated phase of 720 degrees is obtained as the linear interpolation of the OCT signal between phase points [705, 1105] degrees, i.e., a value of the OCT signal obtained by linear interpolation from the OCT signal values of [1.2, 3.4]. The signal at the recalculated phase of 1080 degrees is also obtained as the linear interpolation of the OCT signal between phase points [705, 1105] degrees, i.e., a value of the OCT signal obtained by linear interpolation from the OCT signal values of [1.2, 3.4], but this time corresponding to phase point of 1080 degrees. And finally, the signal at the recalculated phase of 1440 degrees is obtained as the linear interpolation of the OCT signal between phase points [1105, 1605] degrees, i.e., a value of the OCT signal obtained by linear interpolation from the OCT signal values of [3.4, −5.6]. As seen above, the obtained phase values (in degrees) being divisible by 360 degrees yields integer phase values in radians. Specifically, [1, 2, 3, 4] corresponding to the phase values [360, 720, 1080, and 1440] degrees. In other words, the phase points of interest at which the values of OCT are to be resampled or interpolated may be obtained by finding the integer crossing of the phase point values (in radians) within the range of phase point values represented or defined by the recalculated phase values.

If the phase oversample factor is chosen as 6, the recalculated phase values are: [41*6, 81*6, 141*6, 221*6, 321*6] degrees=[246, 486, 846, 1326, 1926] degrees. In the range of recalculated phase point values, the phase values of interest are: [360, 720, 1080, 1440, 1800] degrees. Phase values of interest may be similarly obtained for any selected interpolation factor (or phase oversample factor). It should be noted that in the above examples, two resample points are evaluated between phase values 705 degrees and 1105 degrees, and phase values 1326 degrees and 1926 degrees, respectively. In order to perform real-time computation, two or three linear interpolators may be operated in parallel to sustain throughput. The choice of phase oversample (or interpolation) factor may be dependent on the laser, and is typically configured by the user, and may be application specific. In general, frequency sweep of a laser is constant, but the jitter of the laser source may need to be taken into consideration, as it may present a problem in OCT. In order to extract the phase of the K-Clock, the analog K-Clock signal may be sampled or digitized using an ADC. Once the K-Clock has been digitized, the phase of the digitized K-Clock may be extracted using the Hilbert Transform.

One embodiment of an architecture implementing the resampling technique described above is shown in FIG. 9. The Hilbert Transform is implemented as an FIR (finite impulse response) filter 904 to enable real-time processing. A matched delay 902 ensures that the Real and Imaginary component of the K-Clock signal are in sync at phase extraction block 906. Similarly, a matched delay 903 ensures that the OCT signal and sampling output signal are in sync at linear interpolation block 912. The K-Clock signal may be received from a signal generator circuit (not shown) that generates the analog chirp signal, digitizes the analog chirp signal, and provides the digitized signal to matched delay component 902 and filter component 904. Phase extraction block 906 may be designed to produce a normalized phase value output, i.e., a phase value in radians. The extracted phase is unwrapped in Phase Unwrap Block 908. The unwrapped phase is multiplied with the specified (designated) Interpolation Factor to obtain the recalculated phase points, which are provided to integer crossing block 910 to obtain/determine the phase point values divisible by 360 degrees. In embodiments where phase extraction block 906 provides normalized phase values in radians to integer crossing block 910, integer crossing block 910 may assert a control signal output (indicative that resampling or interpolation is to take place) each time the phase value is an integer value. The output from integer crossing block 910 is thus provided to the Linear Interpolation block 912 to obtain the corresponding resampled value of the OCT signal. Implementing the Hilbert Transform as an FIR filter has at least two additional advantages besides enabling real-time processing. The Hilbert FIR Filter block 904 provides a 90-degree phase shift, and the filter's characteristics operate to reduce distortion and noise in the K-Clock signal.

Figure 9:
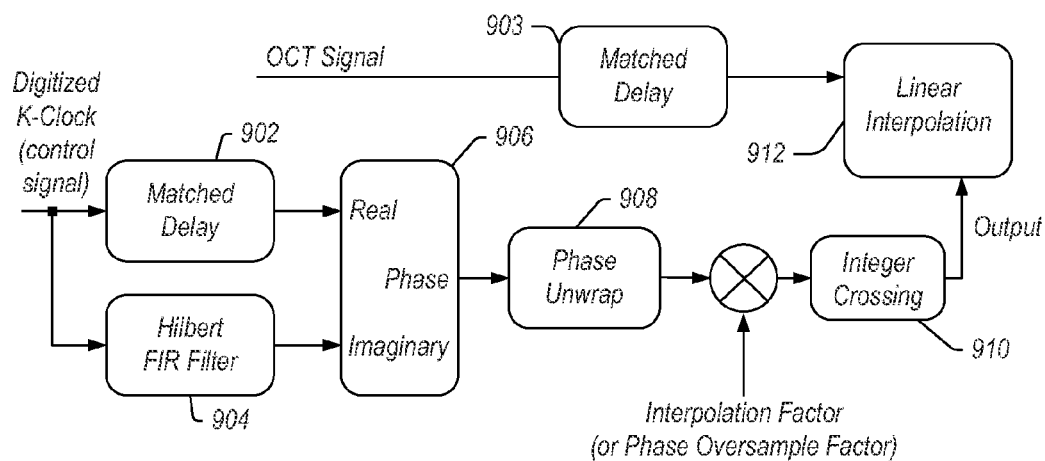
FIG. 9 shows a function diagram illustrating operation of one embodiment of an OCT system that performs resampling.
Figure 10:
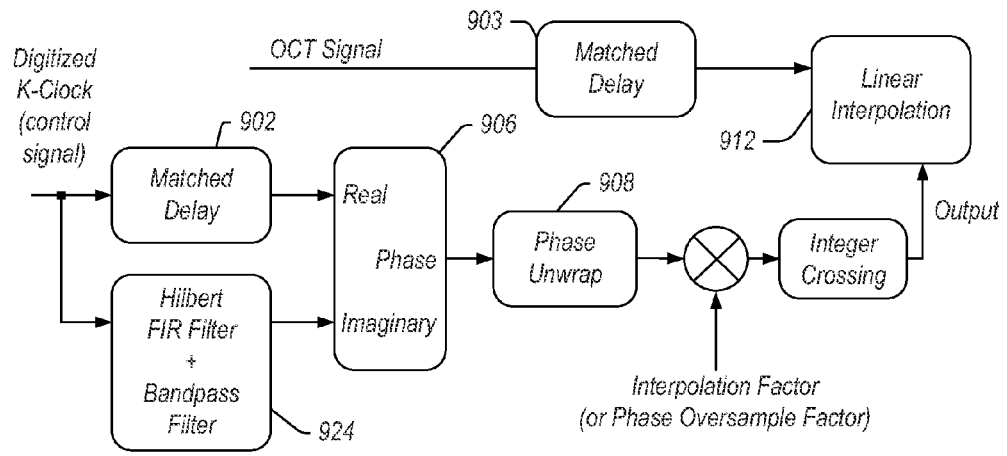
FIG. 10 shows a function diagram illustrating the operation of the embodiment of the OCT system from FIG. 9, with bandpass filtering combined with the Hilbert Transform filter.
Figure 11:
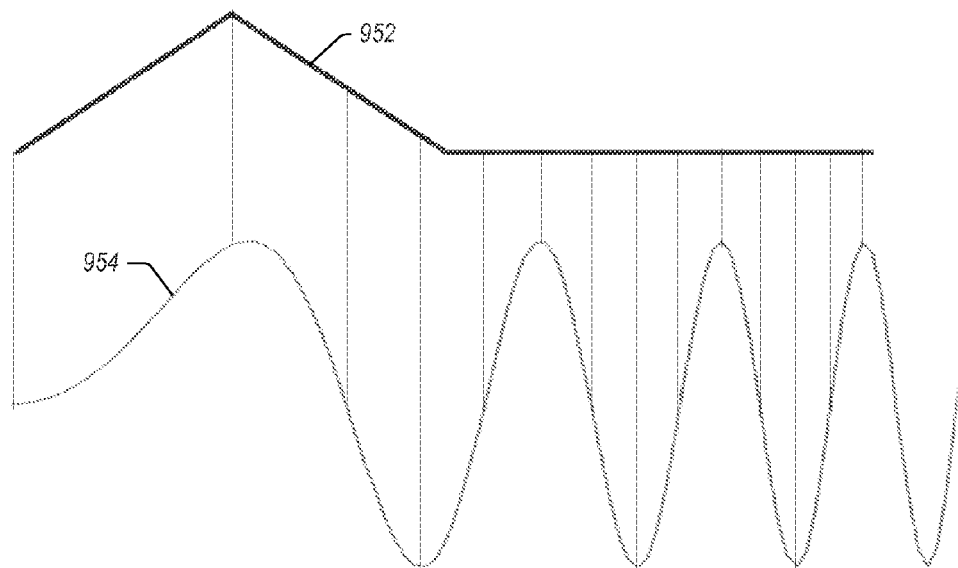
FIG. 11 shows a signal diagram illustrating resampling of an OCT signal with a resampling factor of 4.

FIG. 10 shows a slightly modified version of the implementation illustrated in FIG. 9. In the implementation shown in FIG. 10, a bandpass filter and 90-degree phase shifter is combined into a single processing block 924, in other words the bandpass filtering and 90-degree phase shifting is combined into a single step, which lowers the latency of computation, and improves the accuracy of the phase information extracted from the K-Clock signal. As previously mentioned, the OCT signal is delayed to match the Hilbert Filter (904/924) delay, which facilitates implementing the solutions shown in FIG. 9 and FIG. 10 on an FPGA. The diagram in FIG. 11 shows the OCT signal 952 and K-Clock signal 954 when extracting (resampling) the OCT signal with a phase interpolation factor of 4, according to the implementation shown in FIG. 10. The dashed lines indicate which data points on the OCT signal 952 curve are resampled/interpolated at corresponding phase points on the analog K-Clock 954 curve.

Figure 12:
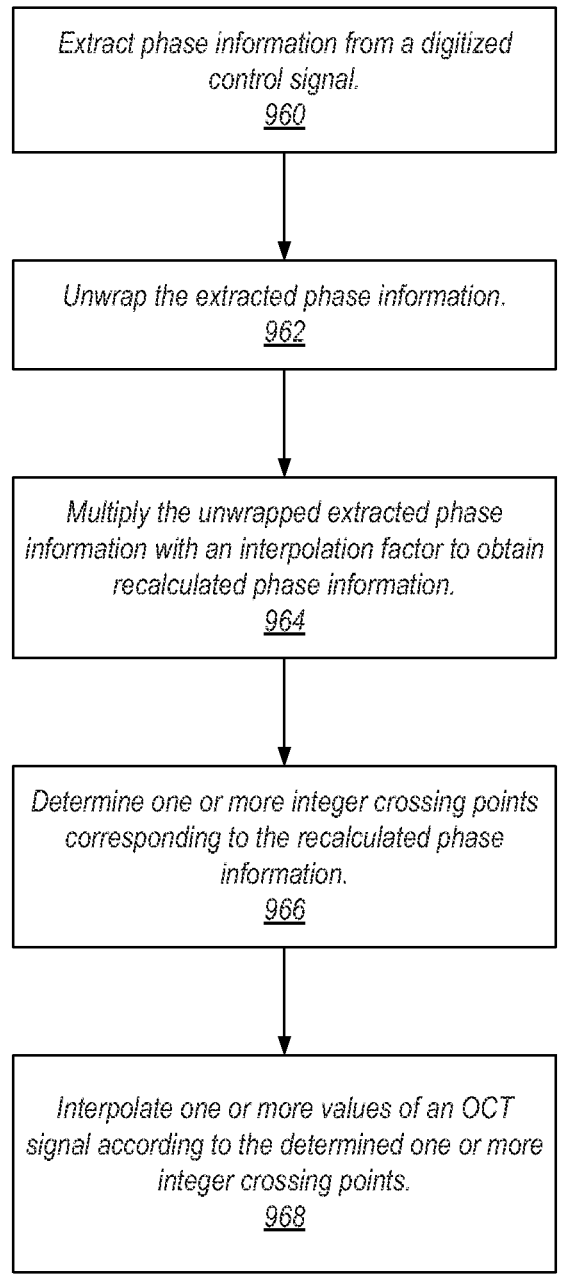
FIG. 12 shows a flow diagram of a method to resample an OCT signal according to one embodiment.

FIG. 12 shows a flow diagram of a method for performing real-time resampling of a data signal, which may be an OCT signal, according to one embodiment. Phase information may be extracted from a control signal, which may be a low-frequency discrete signal (960). The extracted phase information may be unwrapped (962), and the unwrapped extracted phase information may be multiplied with an interpolation factor to obtain recalculated phase information (964). One or more integer crossing points corresponding to the recalculated phase information may then be obtained (966), and one or more values of the OCT signal may be interpolated according to the determined one or more integer crossing points (i.e. according to the one or more normalized phase values that are integers).

Figure 13:
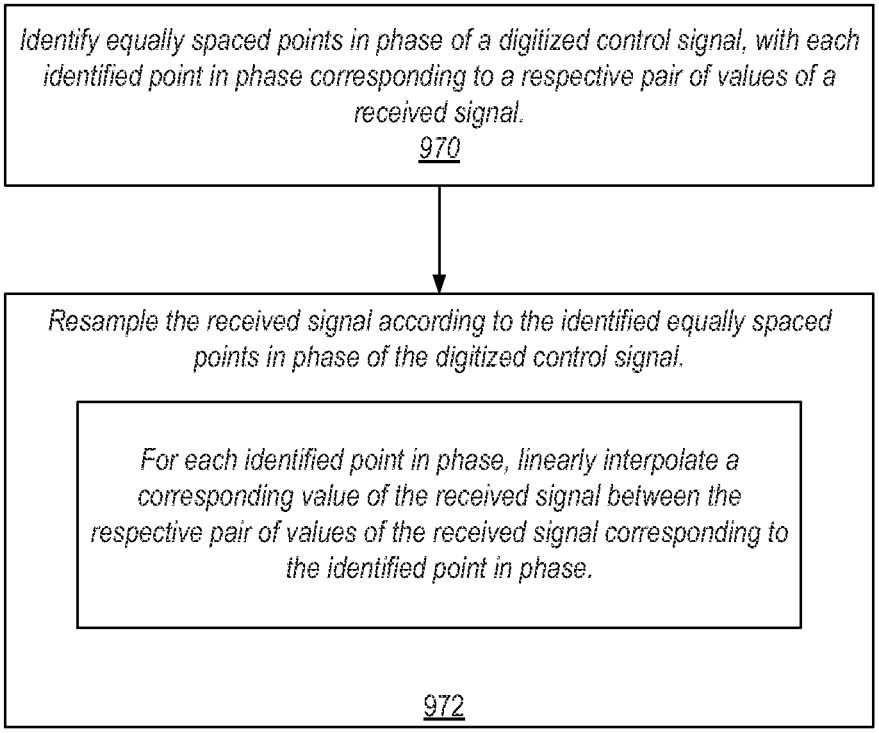
FIG. 13 shows a flow diagram of a method to resample an OCT signal according to another embodiment.

FIG. 13 shows a flow diagram of a method for performing real-time resampling of a received signal, which may be an OCT signal, according to another embodiment. As shown in the flow diagram of FIG. 13, equally spaced points in phase of a digitized control signal, e.g. a digitized K-Clock signal may be identified, with each identified point in phase corresponding to a respective pair of values of the received signal (970). The received signal may be resampled according to the identified equally spaced points in phase of the digitized control signal (972). Resampling the received signal may include, for each identified point in phase, linearly interpolating a corresponding value of the received signal between the respective pair of values of the received signal corresponding to the identified point in phase (972).

As previously mentioned, advantages of various embodiments of an SS-OCT system using a low-frequency K-Clock to resample the OCT signal in real-time eliminates the need for a high-frequency K-Clock, which is currently required in systems intended to perform imaging at deeper axial depths within tissues and materials. The ability to perform real-time processing with low latency for resampling makes it possible to efficiently implement an SS-OCT system on embedded platforms, such as an FPGA. Accordingly, the need for additional hardware circuitry to implement the K-Clock as an external clock for performing analog to digital conversion is also eliminated.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. A method for performing optical coherence tomography (OCT), the method comprising:
   receiving a control signal at a processing device;
   receiving an OCT signal at the processing device;
   extracting, by the processing device, phase information of the received control signal;
   unwrapping, by the processing device, the extracted phase information;
   multiplying, by the processing device, the unwrapped extracted phase information with an interpolation factor to obtain recalculated phase information;
   determining, by the processing device, one or more integer crossing points corresponding to the recalculated phase information;
   interpolating, by the processing device, one or more values of the received OCT signal according to the determined one or more integer crossing points; and
   outputting a sampled version of the received OCT signal according to the interpolated one or more values of the received OCT signal.

2. The method of claim 1, wherein the control signal is a discrete signal;
   wherein the method further comprises generating the control signal by digitizing an analog signal that has varying frequency in time.

3. The method of claim 1, wherein said extracting the phase information of the received control signal comprises filtering the control signal.

4. The method of claim 3, wherein said filtering the received control signal comprises one or more of:
   performing a Hilbert transformation on the received control signal;
   phase shifting the received control signal; or
   reducing distortion and noise in the received control signal.

5. The method of claim 1, further comprising performing said extracting, said unwrapping, said multiplying, said determining, and said interpolating in real-time.

6. A field programmable gate array (FPGA) comprising:
   a plurality of logic circuits interconnected to:
   receive a control signal;
   receive an incoming signal;
   extract normalized phase information from the received control signal;
   unwrap the extracted normalized phase information;
   multiply the unwrapped extracted normalized phase information with an interpolation factor to obtain recalculated phase information;
   determine one or more integer values within a range of phase values defined by the recalculated phase information;
   interpolate one or more values of the received incoming signal according to the identified one or more integer values; and
   output a sampled version of the received incoming signal according at least to the interpolated one or more values of the received incoming signal.

7. The FPGA of claim 6, wherein the control signal is a discrete signal representative of an analog signal having varying frequency with time.

8. The FPGA of claim 6, wherein the plurality of logic circuits are further interconnected to:
   extract the phase information from the received control signal by filtering the received control signal.

9. The FPGA of claim 8, wherein as part of filtering the received control signal, the plurality of logic circuits are further interconnected to perform one or more of the following:
   a Hilbert transformation on the received control signal;
   phase shifting the received control signal; or
   reducing distortion and noise in the received control signal.

10. A method for processing a data signal, the method comprising:
   receiving, at a processing circuit, a control signal representative of an analog signal that has varying frequency in time;

receiving, at the processing circuit, a data signal;
determining, by the processing circuit, equally spaced points in phase of the received control signal, wherein each identified point in phase of the identified equally spaced points in phase corresponds to a respective pair of values of the received control signal;
resampling, by processing circuit, the received data signal according to the identified equally spaced points in phase of the received control signal, said resampling comprising:
for each identified point in phase, linearly interpolating, by the processing circuit a corresponding value of the received data signal between the respective pair of values of the received data signal corresponding to the identified point in phase; and
outputting a sampled version of the received data signal according at least to the interpolated corresponding values of the received data signal.

11. The method of claim 10, wherein said determining comprises:
extracting phase information from the received control signal;
obtaining points in phase from the extracted phase information;
multiplying each obtained point in phase of the obtained points in phase with an interpolation factor to obtain recalculated points in phase, wherein the recalculated points in phase define a range of recalculated points in phase; and
determining desired points in phase within the range of recalculated points in phase, wherein each desired point of the desired points in phase:
is evenly divisible by a specified number; and
has a value that falls between respective values of a corresponding pair of recalculated points in phase within the range of recalculated points in phase;
wherein the identified desired points in phase are the identified equally spaced points in phase.

12. The method of claim 11, wherein the specified number is 360 degrees.

13. The method of claim 10, further comprising:
generating the analog signal using an interferometer and a balanced detector; and
obtaining the control signal by digitizing the analog signal.

14. The method of claim 10, wherein said determining comprises filtering the received control signal.

15. The method of claim 14, wherein said filtering the received control signal comprises one or more of the following:
performing a Hilbert transformation on the received control signal;
phase shifting the received control signal; or
reducing distortion and noise in the received control signal.

16. The method of claim 10, wherein said determining and said resampling are performed in real-time.

17. The method of claim 10, wherein said determining comprises performing a portion of said determining concurrently with said resampling.

18. A system comprising:
a first input configured to receive a control signal;
a second input configured to receive an incoming signal;
a first logic circuit configured to extract phase information from the received control signal;
a second logic circuit configured to obtain phase points from the extracted phase information;
a third logic circuit configured to multiply each obtained phase point of the obtained phase points with an interpolation factor to obtain recalculated phase points;
a fourth logic circuit configured to determine desired phase points within a range defined by the recalculated phase points, wherein each desired phase point of the desired phase points:
is evenly divisible by a specified number; and
has a value that falls between respective values of a corresponding pair of recalculated phase points within the range defined by the recalculated phase points; and
a fifth logic circuit configured to resample the received incoming signal according to the identified desired phase points, and output a sampled version of the received incoming signal according to at least the resampled received incoming signal.

19. The system of claim 18, wherein the first logic circuit comprises one or more of:
a Hilbert Transform finite impulse response filter; or
a bandpass filter.

20. The system of claim 18, wherein to extract the phase information, the first logic circuit is configured to:
obtain a representation of the received control signal as a complex-function;
obtain the phase information based on an imaginary component of the representation of the received control signal and a delayed version of the received control signal.

21. The system of claim 18, further comprising:
additional circuitry configured to generate the control signal.

22. The system of claim 21, wherein the additional circuitry comprises:
a first signal generator configured to generate an analog signal having varying frequency with time; and
an analog-to-digital converter configured to generate the control signal by digitizing the analog signal.

23. The system of claim 18, wherein the incoming signal is an optical coherence tomography (OCT) signal.

24. The system of claim 18, wherein the first, second, third, fourth, and fifth logic circuits are configured on a field programmable gate array (FPGA).

25. The system of claim 24, further comprising:
additional circuitry external to the FPGA, and configured to generate the control signal.

26. The system of claim 18, wherein the first, second, third, fourth, and fifth logic circuits are configured to operate in real-time.

* * * * *